US00PP28915P3

(12) United States Plant Patent
Beekenkamp

(10) Patent No.: US PP28,915 P3
(45) Date of Patent: Jan. 30, 2018

(54) ***DAHLIA* PLANT NAMED 'BKDAMDR'**

(50) Latin Name: *Dahlia hybrida*
Varietal Denomination: BKDAMDR

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 37 days.

(21) Appl. No.: 14/999,406

(22) Filed: May 3, 2016

(65) Prior Publication Data

US 2017/0325380 P1 Nov. 9, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Keith Robinson
(74) *Attorney, Agent, or Firm* — C. A. Whealy

(57) ABSTRACT

A new and distinct cultivar of *Dahlia* plant named 'BKDAMDR', characterized by its broadly upright plant habit; freely basal branching habit; dense and bushy growth habit; medium-sized dark green-colored leaves; and large semi-double inflorescences with dark red-colored ray florets.

2 Drawing Sheets

Botanical designation: *Dahlia hybrida.*
Cultivar denomination: 'BKDAMDR'.

BACKGROUND OF THE INVENTION

The present invention relates to a new and distinct cultivar of *Dahlia* plant, botanically known as *Dahlia hybrida* and hereinafter referred to by the name 'BKDAMDR'.

The new *Dahlia* plant is a product of a planned breeding program conducted by the Inventor in Maasdijk, The Netherlands. The objective of the breeding program is to create new sturdy container *Dahlia* plants that have a freely basal branching habit, and large inflorescences with attractive ray floret coloration.

The new *Dahlia* plant originated from an open-pollination in October, 2011 in Maasdijk, The Netherlands of *Dahlia hybrida* 'BKDARD', disclosed in U.S. Plant Pat. No. 22,929, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Maasdijk, The Netherlands in May, 2012.

Asexual reproduction of the new *Dahlia* plant by terminal cuttings in a controlled greenhouse environment in Maasdijk, The Netherlands since October, 2012 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMDR'. These characteristics in combination distinguish 'BKDAMDR' as a new and distinct *Dahlia* plant:

1. Broadly upright plant habit.
2. Freely basal branching habit; dense and bushy growth habit.
3. Medium-sized dark green-colored leaves.
4. Large semi-double inflorescences with dark red-colored ray florets.

Plants of the new *Dahlia* differ primarily from plants of the female parent, 'BKDARD', in the following characteristics:

1. Plants of the new *Dahlia* are smaller than plants of 'BKDARD'.
2. Plants of the new *Dahlia* and 'BKDARD' differ in ray floret color as plants of 'BKDARD' have bright red-colored ray florets.
3. Plants of the new *Dahlia* have shorter peduncles than plants of 'BKDARD'.

Plants of the new *Dahlia* can be compared to plants of *Dahlia variabilis* 'Ruicaro', disclosed in U.S. Plant Pat. No. 11,566. In side-by-side comparisons, plants of the new *Dahlia* differ from plants of 'Ruicaro' in the following characteristics:

1. Plants of the new *Dahlia* have slightly smaller inflorescences than plants of 'Ruicaro'.
2. Plants of the new *Dahlia* and 'Ruicaro' differ in ray floret color as plants of 'Ruicaro' have bright red-colored ray florets.
3. Plants of the new *Dahlia* and 'Ruicaro' differ in anther and pollen color as plants of 'Ruicaro' have more yellow-colored anthers and pollen.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAMDR' grown in a container.

The photograph on the second sheet is a close-up view of a typical inflorescence of 'BKDAMDR'.

DETAILED BOTANICAL DESCRIPTION

The aforementioned photographs and the following observations and measurements describe plants grown during the winter in 12-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks old when the photographs and description were taken. To induce inflorescence initiation and development, plants were grown under short nyctoperiod (long day) conditions. In the following description, color references are made to The Royal Horticultural Society Colour Chart, 2015 Edition, except where general terms of ordinary dictionary significance are used.

Botanical classification: *Dahlia hybrida* 'BKDAMDR'.

Parentage:

- *Female, or seed, parent.*—*Dahlia hybrida* 'BKDARD', disclosed in U.S. Plant Pat. No. 22,929.
- *Male, or pollen, parent.*—Unknown selection of *Dahlia hybrida*, not patented.

Propagation:

- *Type.*—By terminal cuttings.
- *Time to initiate roots, summer.*—About 16 days at temperatures ranging from 18° C. to 21° C.
- *Time to initiate roots, winter.*—About 19 days at temperatures ranging from 19° C. to 21° C.
- *Time to produce a rooted young plant, summer.*—About 21 days at temperatures ranging from 18° C. to 21° C.
- *Time to produce a rooted young plant, winter.*—About 23 days at temperatures ranging from 19° C. to 21° C.
- *Root description.*—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia.*
- *Rooting habit.*—Moderately freely branching; medium density.

Plant description:

- *Plant and growth habit.*—Broadly upright and mounding plant form; overall plant shape, flattened globular; freely basal branching habit with about four primary branches developing per plant; inflorescences held above the foliar plane on strong peduncles; bushy and dense growth habit; pinching is not required but will improve branching habit; moderately vigorous growth habit.
- *Plant height, soil level to top of foliar plane.*—About 13.9 cm.
- *Plant height, soil level to top of floral plane.*—About 19 cm.
- *Plant diameter or spread.*—About 29.1 cm.
- *Lateral branches.*—Length: About 8.7 cm. Diameter: About 6 mm. Internode length: About 1.2 cm. Aspect: Primary branches are mostly erect; secondary branches, about 40° from primary branch axis. Strength: Moderately strong. Texture and luster: Smooth, glabrous; glossy. Color, developing: Close to N186C. Color, developed: Close to 143B to 143C tinged with close to N186C.

Leaf & leaflet description:

- *Arrangement.*—Leaves opposite and compound with five leaflets.
- *Length, leaves.*—About 10.9 cm.
- *Length, terminal leaflets.*—About 7.2 cm.
- *Width, leaves.*—About 11.8 cm.
- *Width, terminal leaflets.*—About 4.6 cm.
- *Shape, leaves in overall outline.*—Broadly ovate to roughly triangular.
- *Shape, leaflets.*—Broadly elliptic.
- *Apex, leaflets.*—Acute to slightly apiculate.
- *Base, leaflets.*—Attenuate.
- *Margin, leaflets.*—Coarsely serrate to dentate.
- *Venation pattern, leaflets.*—Pinnate.
- *Texture and luster, upper surface, leaflets.*—Slightly rugose, sparsely pubescent; slightly velvety; slightly glossy.
- *Texture and luster, lower surface, leaflets.*—Smooth, sparsely pubescent; slightly glossy.
- *Color.*—Developing leaflets, upper surface: Close to between 139A and N189A. Developing leaflets, lower surface: Close to 189A. Fully expanded leaflets, upper surface: Slightly darker than between NN137A and 147A; venation, close to between 189A and 191A. Fully expanded leaflets, lower surface: Close to 143A; venation, close to 146A.
- *Petioles.*—Length: About 3.1 cm. Width: About 4.5 mm. Height: About 4 mm. Strength: Moderately strong to strong. Texture and luster, upper and lower surfaces: Smooth, glabrous; glossy. Color, upper surface: Close to 144A strongly tinged with close to 187A. Color, lower surface: Close to 146B to 146C slightly tinged with close to 187A.

Inflorescence description:

- *Appearance and arrangement.*—Semi-double inflorescence form with ray and disc florets forming acropetally on a receptacle; inflorescences positioned above and beyond the foliar plane on strong peduncles; inflorescences face mostly upright to slightly outwardly; freely flowering habit with about 30 inflorescences developing per plant.
- *Fragrance.*—None detected.
- *Flowering response and flowering period.*—Early flowering habit, plants begin flowering about 61 days after planting; plants flower continuously during the autumn into the winter in The Netherlands.
- *Post-production longevity.*—Inflorescences maintain good substance for about ten days on the plant; inflorescences persistent.
- *Inflorescence buds.*—Height: About 9 mm. Diameter: About 1.5 cm. Shape: Flattened globular. Texture and luster: Smooth, glabrous; glossy. Color: Close to 144C; towards the base, close to 143B to 143C and tinged with close to 178B to 178C.

*Inflorescence size*.—Diameter: About 7.5 cm. Depth (height): About 6 cm. Disc diameter: About 1.9 cm.

*Receptacles*.—Height: About 2 mm. Diameter: About 8 mm. Shape: Flattened globular. Color: Close to 145B to 145C.

*Ray florets*.—Quantity per inflorescence and arrangement: About 120 arranged in about six whorls. Length: About 3.4 cm. Width: About 1.7 cm. Shape: Obovate. Apex: Obtuse to shallowly retuse. Base: Attenuate. Margin: Entire. Aspect: Upright to roughly horizontal and eventually downward; moderately to strongly concave. Texture and luster, upper surface: Smooth, glabrous; velvety; slightly glossy. Texture and luster, lower surface: Smooth, glabrous; velvety; matte. Color: When opening, upper surface: More intense and darker than between 53A and 59A. When opening, lower surface: Close to 59B and towards the apex, close to 53A. Fully opened, upper surface: More intense and darker than 53A; venation, same as lamina, more intense and darker than 53A; color does not change with development. Fully opened, lower surface: Close to 53A and towards the base, close to 60C to 60D; venation, close to 63A; colors do not change with development.

*Disc florets*.—Quantity per inflorescence and arrangement: About 50 massed at the center of the inflorescence in about five spiral whorls. Length: About 1.4 cm. Diameter: About 6 mm. Shape: Tubular, elongated; apices, acute. Texture and luster, inner and outer surfaces: Smooth, glabrous; glossy. Color, when opening, inner and outer surfaces: Apex: Close to 13A. Mid-section: Close to 154B. Base: Close to 157D. Color, fully opened, inner and outer surfaces: Apex: Close to 13A. Mid-section: Close to 154B. Base: Close to 157D.

*Phyllaries*.—Quantity per inflorescence and arrangement: About seven arranged in about two whorls. Length: About 1.5 cm. Width: About 6 mm. Shape: Elliptic. Apex: Acute. Base: Cuneate. Margin: Entire. Texture and luster, upper and lower surfaces: Smooth, glabrous; moderately glossy. Color, upper surface: Close to NN137B. Color, lower surface: Close to NN137B to NN137C.

*Peduncles*.—Length, terminal peduncle: About 6.7 cm. Diameter, terminal peduncle: About 3 mm. Strength: Strong. Texture and luster: Smooth, glabrous; moderately glossy. Color: Close to 146B strongly tinged with close to 200C.

*Reproductive organs*.—Androecium, present on disc florets only: Quantity per floret: About five. Filament length: About 3 mm. Filament color: Close to 150C. Anther shape: Narrowly oblong. Anther length: About 4 mm. Anther color: Close to 16A. Pollen amount: Abundant. Pollen color: Close to 23A. Gynoecium, present on disc florets only: Quantity per floret: One. Pistil length: About 1.3 cm. Style length: About 1 cm. Style color: Close to 150C. Stigma diameter: About 6 mm. Stigma shape: Cleft, decurrent. Stigma color: Close to 17A to 17B. Ovary color: Close to 145D. Seeds and fruits: Seed and fruit development have not been observed on plants of the new *Dahlia*.

Disease & pest resistance: Plants of the new *Dahlia* have not been observed to be resistant to pathogens and pests common to *Dahlia* plants.

Temperature tolerance: Plants of the new *Dahlia* have been observed to tolerate high temperatures of about 35° C. and to be suitable for USDA Hardiness Zones 9 to 11.

It is claimed:

1. A new and distinct *Dahlia* plant named 'BKDAMDR' as illustrated and described.

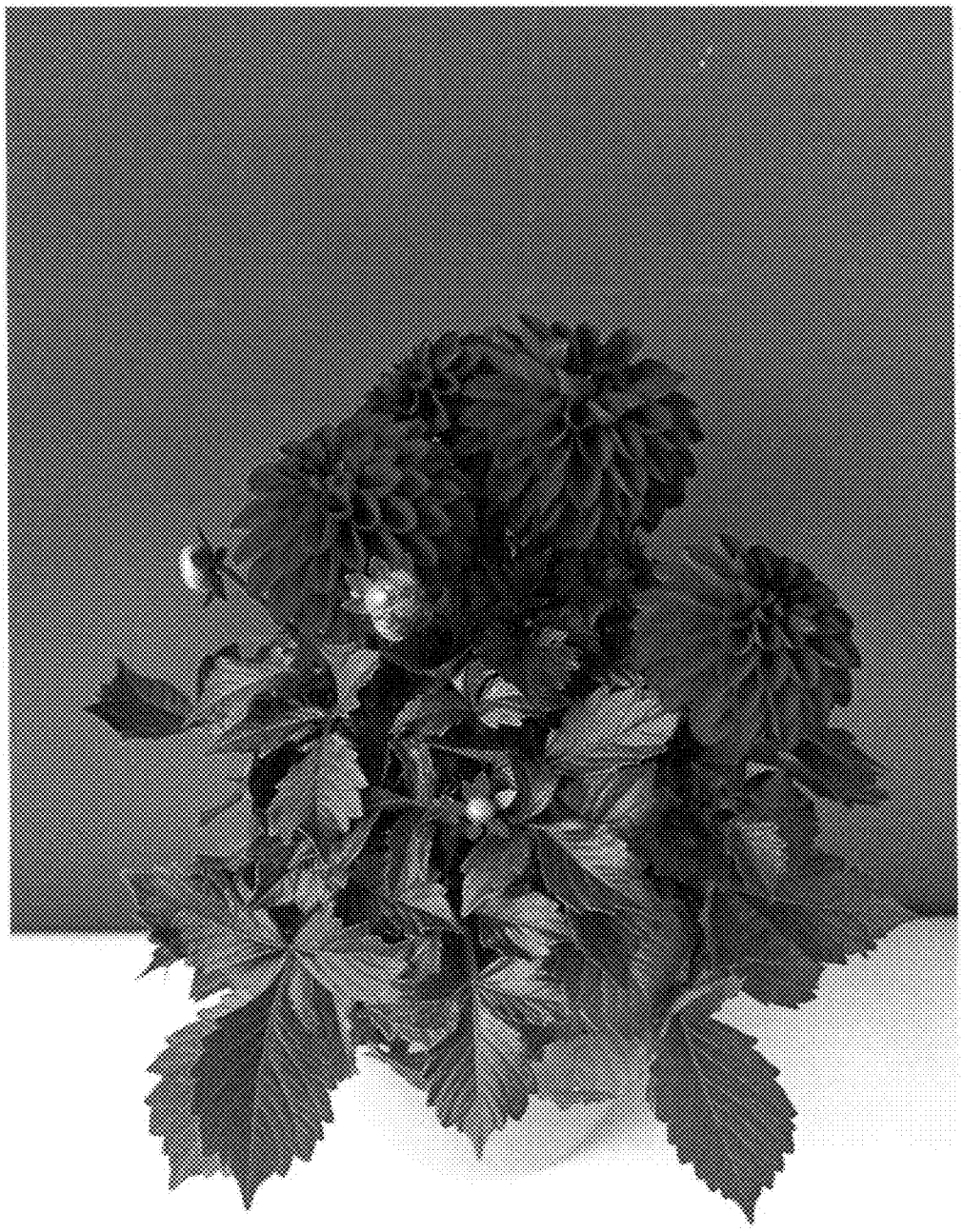

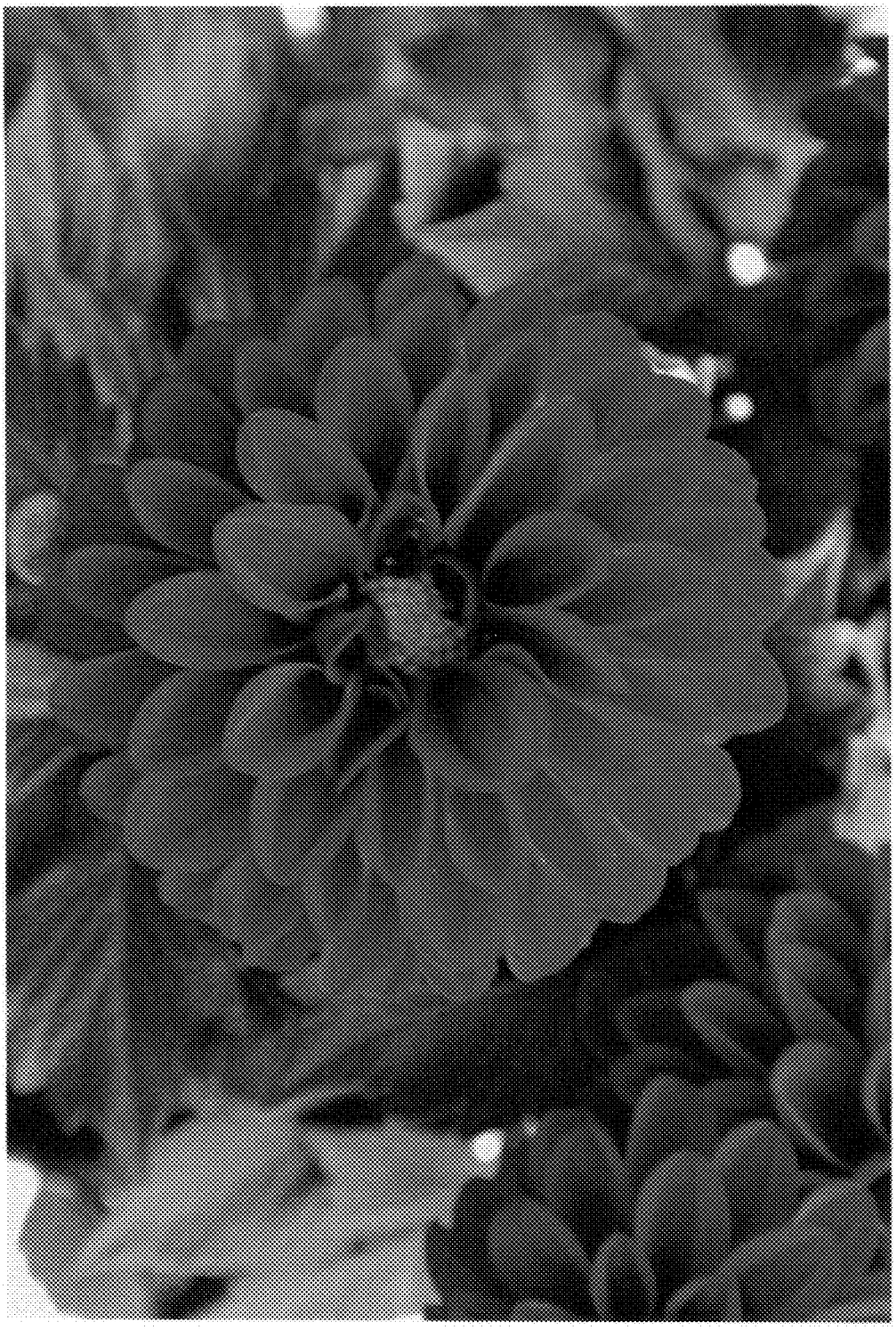

* * * * *